United States Patent
Kim et al.

(10) Patent No.: US 10,441,383 B2
(45) Date of Patent: Oct. 15, 2019

(54) ENDO FILE FOR DENTAL ENDODONTIC TREATMENT

(71) Applicants: Hyeong Woo Kim, Seongnam-si (KR); Gyun Hwan Kim, Goyang-si (KR); Sun Young Kim, Goyang-si (KR)

(72) Inventors: Hyeong Woo Kim, Seongnam-si (KR); Gyun Hwan Kim, Goyang-si (KR); Sun Young Kim, Goyang-si (KR)

( * ) Notice: Subject to any disclaimer, the term of this patent is extended or adjusted under 35 U.S.C. 154(b) by 0 days.

(21) Appl. No.: 14/898,180

(22) PCT Filed: Aug. 1, 2013

(86) PCT No.: PCT/KR2013/006971
§ 371 (c)(1),
(2) Date: Dec. 14, 2015

(87) PCT Pub. No.: WO2014/200146
PCT Pub. Date: Dec. 18, 2014

(65) Prior Publication Data
US 2016/0128800 A1    May 12, 2016

(30) Foreign Application Priority Data

Jun. 14, 2013 (KR) .................. 10-2013-0068299
Jul. 30, 2013 (KR) .................. 10-2013-0090285

(51) Int. Cl.
*A61C 5/00* (2017.01)
*A61C 5/48* (2017.01)
*A61C 5/42* (2017.01)

(52) U.S. Cl.
CPC . *A61C 5/48* (2017.02); *A61C 5/42* (2017.02)

(58) Field of Classification Search
CPC .......... A61C 5/028; A61C 5/026; A61C 5/42; A61C 5/44; A61C 5/46; A61C 5/48
USPC ...... 433/81, 102, 224, 165, 166, 32; 606/80; 408/199–233; 175/327–435; 451/527–539
See application file for complete search history.

(56) References Cited

U.S. PATENT DOCUMENTS

| | | | | |
|---|---|---|---|---|
| 1,327,149 A | * | 1/1920 | Duncan | A61C 5/02 433/102 |
| 3,919,775 A | * | 11/1975 | Malmin | A61C 3/00 433/32 |
| 4,321,040 A | * | 3/1982 | Miller | A61C 5/42 433/102 |
| 4,746,292 A | * | 5/1988 | Johnson | A61C 5/46 294/212 |

(Continued)

FOREIGN PATENT DOCUMENTS

| | | |
|---|---|---|
| JP | 09108914 A * | 4/1997 |
| KR | 1020080090996 | 10/2008 |
| KR | 1020100018914 | 2/2010 |

*Primary Examiner* — Nicholas D Lucchesi
(74) *Attorney, Agent, or Firm* — Jake K. Lee

(57) ABSTRACT

An endo file for dental endodontic treatment includes: a head portion inserted into and detachably coupled to a hand piece; a tissue removing portion inserted, from the lower side of the head piece, into a patient's root canal for removing the nerve of a tooth; and a stress dispersion portion provided between the head portion and the tissue removing portion and having at least one horizontal penetration hole so as to buffer stress concentration generated during the rotation of the endo file, and to minimize endo file breakage.

5 Claims, 6 Drawing Sheets

(56) References Cited

U.S. PATENT DOCUMENTS

| | | | | |
|---|---|---|---|---|
| 4,984,985 A * | 1/1991 | Edwardson | | A61C 1/148 433/118 |
| 5,158,405 A * | 10/1992 | Serafin | | B23B 51/101 407/8 |
| 5,505,617 A * | 4/1996 | Skeppmark | | A61C 1/07 433/118 |
| 6,227,855 B1 * | 5/2001 | Hickok | | A61C 5/026 433/141 |
| 6,267,592 B1 * | 7/2001 | Mays | | A61B 17/1615 433/102 |
| 2004/0081940 A1 * | 4/2004 | Roetzer | | A61C 3/02 433/165 |
| 2004/0142302 A1 * | 7/2004 | Aeby | | A61C 5/46 433/141 |
| 2005/0244785 A1 * | 11/2005 | Cox | | A61C 5/42 433/102 |
| 2008/0057468 A1 | 3/2008 | Rosenblood et al. | | |
| 2009/0004621 A1 * | 1/2009 | Quan | | A61C 5/02 433/81 |
| 2009/0035727 A1 * | 2/2009 | Maissami | | A61C 3/005 433/224 |
| 2009/0176188 A1 * | 7/2009 | Tobis | | A61C 5/40 433/102 |
| 2010/0028832 A1 | 2/2010 | Gutzner et al. | | |
| 2011/0111365 A1 * | 5/2011 | Gharib | | A61C 5/40 433/81 |
| 2011/0300503 A1 | 12/2011 | Benvegnu et al. | | |
| 2012/0179161 A1 * | 7/2012 | Rains | | A61B 17/1617 606/80 |
| 2012/0219927 A1 * | 8/2012 | Maxwell | | A61C 5/023 433/102 |
| 2013/0101956 A1 * | 4/2013 | Larsen | | A61C 3/00 433/102 |
| 2013/0122450 A1 * | 5/2013 | Simons | | A61C 5/045 433/27 |
| 2013/0260334 A1 * | 10/2013 | Pernot | | A61C 5/04 433/81 |
| 2013/0302751 A1 * | 11/2013 | Maxa | | A46B 13/008 433/166 |
| 2014/0276840 A1 * | 9/2014 | Richter | | A61B 17/1671 606/80 |

\* cited by examiner

ENDO FILE FOR DENTAL ENDODONTIC TREATMENT

BACKGROUND

The present invention generally relates to an endo file for dental endodontic treatment. More particularly, the present invention relates to an improved endo file for dental endodontic treatment, which includes a head portion connected to a hand piece, a tissue removing portion for removing a nerve of a tooth, and a stress dispersion portion provided between the head portion and the tissue removing portion and having a horizontal penetration hole, wherein the horizontal penetration hole of the stress dispersion portion is configured in various shapes so that the horizontal penetration hole can efficiently disperse torque that is transferred to an end of the endo file during a rotation of the endo file, without allowing concentration of the torque on a specific portion, whereby endo file breakage is minimized during use.

In general, an endo file is a medical tool for removing a nerve of a tooth, wherein the endo file is inserted into an inside of root canal of a tooth lesion for removing a nerve and/or diseased tissue. The endo file is made of an elastic material so as to be bent in response to a shape of a tooth.

The endo file is widely used in dental clinics across the world, wherein the endo file is mounted to a hand piece that rotates automatically by pneumatic power or electric motor.

FIG. 1 is a view showing a conventional endo file 1 described above.

The conventional endo file 1 includes: a head portion 20 detachably coupled to a hand piece 10; a tissue removing portion 30 at a lower part of the head portion 20 for removing a nerve of a tooth; and a connection portion 40 provided between the head portion 20 and the tissue removing portion 30 and functioning as a shape transition part.

According to the conventional endo file 1, when the head portion 20 that is detachably coupled to the hand piece 10 rotates, torque generated during the rotation is transmitted to the tissue removing portion 30, and the tissue removing portion 30 rotates. Thus, endodontic treatment is performed by removing a nerve, a blood vessel, and tissue of a tooth lesion (not shown) using the tissue removing portion 30. In a process of the endodontic treatment, the tissue removing portion of the conventional endo file 1 moves in and out of the root canal of the tooth repeatedly.

However, the conventional endo file 1 is often broken during use, namely during rotation. The breakage of the endo file 1 is caused by following reasons in the state of the tissue removing portion 30 being inserted into the root canal of the tooth: excessive stress occurs on the tissue removing portion 30 due to torque resistance of the nerve and the tissue when the tissue removing portion 30 rotates by the torque transmitted from the head portion 20; excessive stress is generated by rotation of the endo file in a portion of a root canal that is badly crooked; or sudden excessive stress occurs on some part of the endo file when the endo file is tightly caught in the root canal of the tooth.

Further, when treating a tooth located deep in a mouth, both the endo file and the hand piece coupled thereto should be put deep into the mouth. Here, for a patient who cannot open his or her mouth wide, it is highly possible that the tissue removing portion is badly bent and is broken due to a disadvantage of the conventional endo file configured such that the connection portion 40 thereof has very low elasticity in bending.

In particular, breakage or fracture of the endo file usually occurs at a certain section away from an end of the tissue removing portion 30, for example, at a location that is 1~3 mm away from the end. However, it is not easy to modify the shape of the tissue removing portion 30 for removing a nerve and a blood vessel.

As a document of a related art relating to breakage of the conventional endo file, Korean Patent No. 10-1011695 discloses "Endo file for dental endodontic treatment".

The endo file for dental endodontic treatment according to the above-mentioned related art is configured to be capable of easily removing a fragment of the endo file even when the end of the endo file is broken during the endodontic treatment. The endo file according to the related art includes: a tissue removing portion inserted into the inside of root canal of a tooth for removing a nerve and a blood vessel; and a connection portion provided on the tissue removing portion, wherein even when the tissue removing portion is broken due to repetitive use, the connection portion connects an upper part and a lower part of the fractured tissue removing portion together so that the lower part of the fractured tissue removing portion can be removed, along with the upper part, from the tooth.

The endo file for dental endodontic treatment according to the related art is advantageous in that it is possible to predict when a fracture of the tissue removing portion may occur due to repetitive use. Another advantage of the endo file according to the related art resides in that it is possible to prevent a fragment of the fractured tissue removing portion from being caught in the patient's tooth by easily removing an end of the fractured endo file from the tooth.

However, the related art focuses on removing the fractured end of the endo file 1 after the endo file 1 is broken. The related art is not intended to prevent the endo file 1 breakage itself in advance.

SUMMARY OF THE INVENTION

Accordingly, the present invention has been made keeping in mind the above problems occurring in the related art, and the present invention is intended to propose an improved endo file for dental endodontic treatment, the endo file configured such that when the endo file rotates after entering the root canal of a tooth, torque is evenly transmitted from a head portion to an end of a tissue removing portion, and endo file breakage during use can be minimized by efficiently dispersing stress across the endo file.

Further, the present invention is intended to propose an endo file for dental endodontic treatment, the endo file configured to minimize stress concentration on a portion where excessive torque of the endo file primarily occurs, to buffer torque concentration, and to evenly disperse the torque so as to ensure stable rotation of the tissue removing portion without breakage thereof.

Furthermore, the present invention is intended to propose an endo file for dental endodontic treatment, the endo file configured to induce the stress dispersion portion thereof to break when the endo file is broken due to stress concentration, thereby allowing the broken endo file to be easily removed from the root canal of the tooth even when the endo file is broken.

Meanwhile, the present invention is intended to propose an endo file for dental endodontic treatment, the endo file configured such that, when stress large enough to break the endo file is generated during rotation after the endo file has entered the root canal of a tooth, the stress dispersion portion twists so that an operator can recognize the twisting of the stress dispersion portion before breakage of the endo file occurs.

In order to achieve the above object, according to one aspect of the present invention, there is provided an endo file for dental endodontic treatment, the endo file including: a head portion inserted into and detachably coupled to a hand piece; a tissue removing portion inserted, from a lower side of the head portion, into an inside of a root canal of a patient's tooth for removing a nerve of the tooth; and a stress dispersion portion provided between the head portion and the tissue removing portion and having at least one horizontal penetration hole therein so as to prevent and buffer stress concentration during a rotation of the endo file and to minimize endo file breakage.

Further, in the present invention, the endo file may be configured such that the horizontal penetration hole provided in the stress dispersion portion has a quadrilateral, polygonal, cruciform or oval cross-section shape.

Furthermore, in the present invention, the endo file may be configured such that the horizontal penetration hole includes two to four horizontal penetration holes formed in a circumferential direction of a cross-section of the endo file while being spaced out at equal intervals.

According to an endo file for dental endodontic treatment of the present invention, it is possible to prevent stress concentration that is generated when the endo file rotates in a root canal by providing a stress dispersion portion in a connection portion between a head portion and a tissue removing portion and having at least one horizontal penetration hole therein.

In other words, the stress dispersion portion provided in a lower part of the head portion divides the cross-section thereof into more than one section due to at least one horizontal penetration hole horizontally penetrating through the connection portion. Further, when the endo file rotates in the root canal of a tooth, the stress dispersion portion prevents the stress from being concentrated on a portion of the endo file. In addition, the stress dispersion portion evenly transmits torque from the head portion to an end of the tissue removing portion, and thereby it is possible to efficiently prevent the endo file from breaking.

In particular, the stress dispersion portion minimizes the stress concentration due to a division of the cross-section of the connection portion when large torque transferred from the head portion, which is coupled to a hand piece and is rotated, is primarily transmitted to the connection portion. In addition, the stress dispersion portion stably rotates the endo file while not breaking the endo file by equally dispersing the torque across the cross-section thereof, and efficiently transmits the torque to the tissue removing portion. Therefore, the endo file is useful for effective dental endodontic treatment.

Further, even when enough stress is generated to break the endo file after the endo file has entered the root canal of the tooth, the stress dispersion portion twists so that an operator can recognize a twisted stress dispersion portion before the endo file breaks.

DETAILED DESCRIPTION OF THE INVENTION

Reference will now be made in greater detail to an endo file for dental endodontic treatment according to an exemplary embodiment of the present invention with reference to the accompanying drawings.

Figure 1:
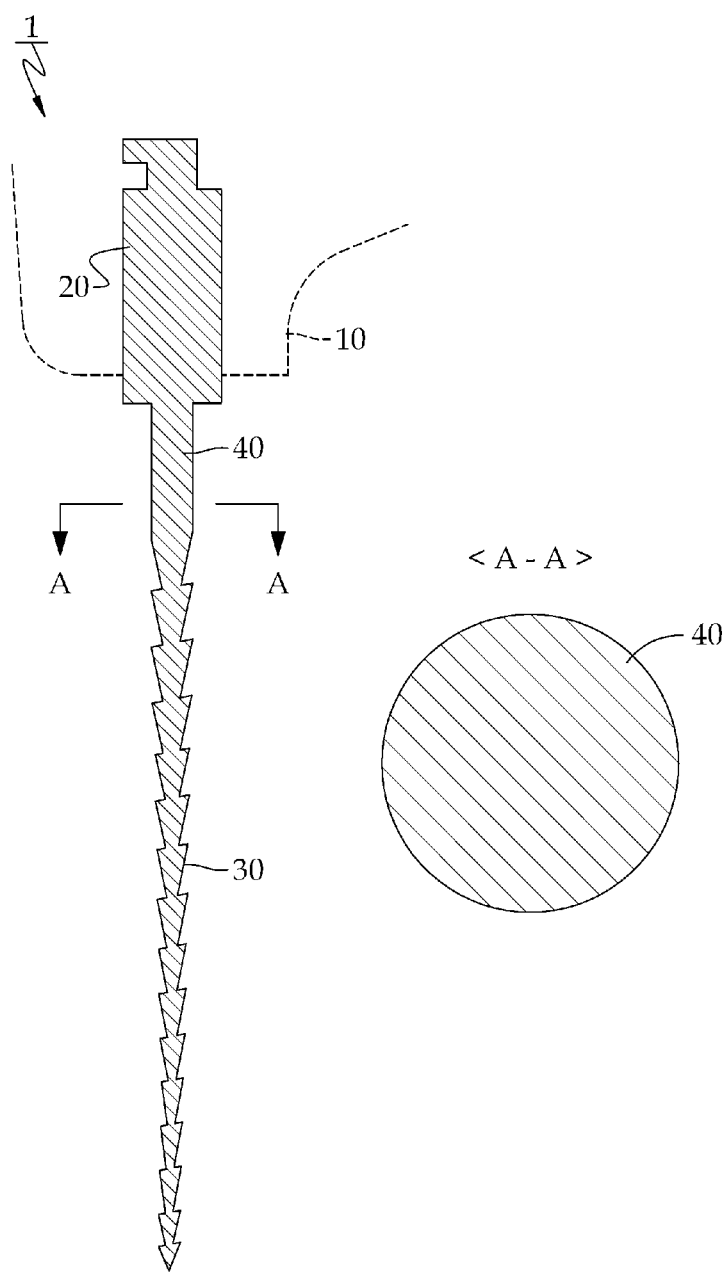
FIG. 1 is a sectional view showing a structure of a conventional endo file.
Figure 2:
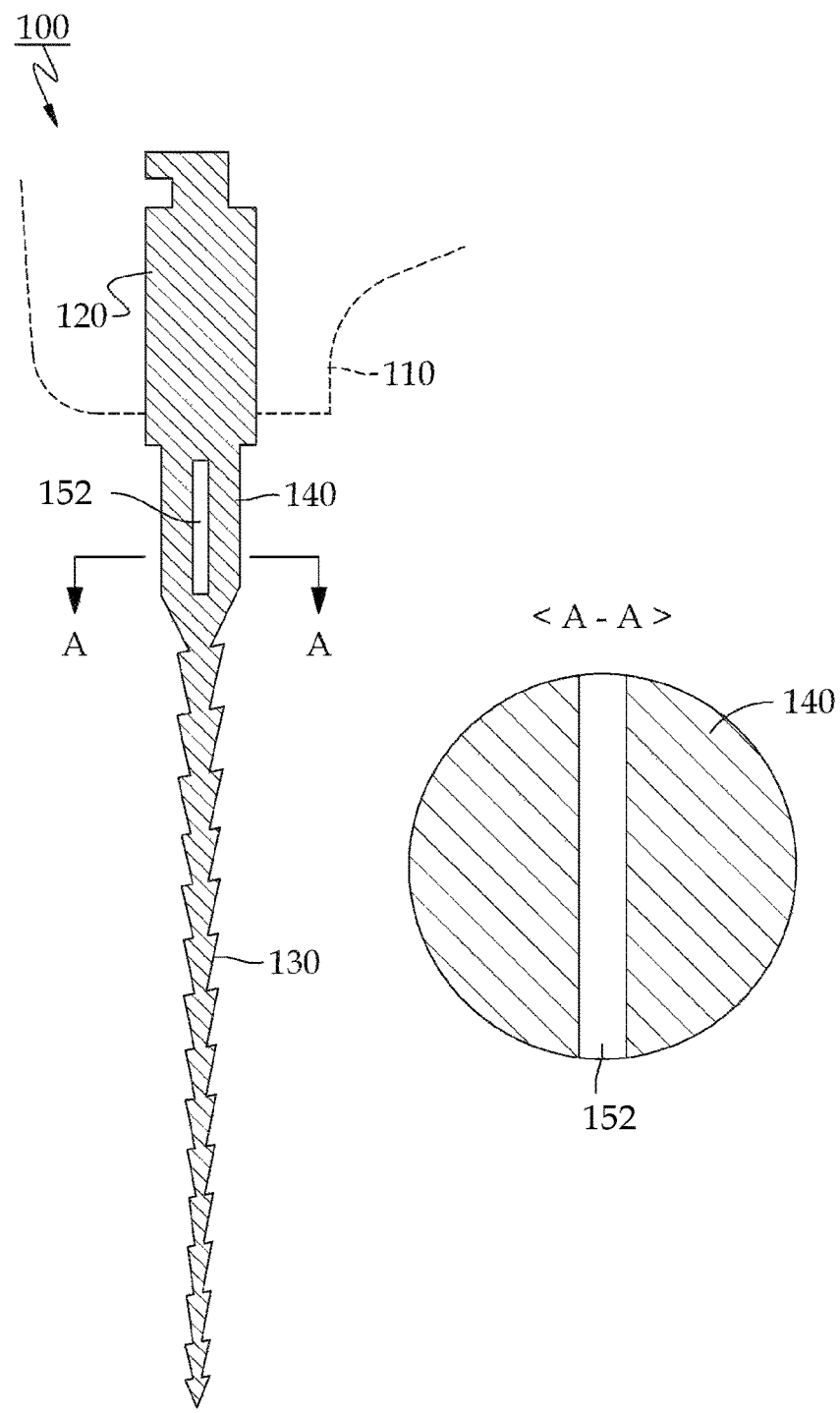
FIG. 2 is a sectional view showing a structure of an endo file according to the present invention that includes a stress dispersion portion having a horizontal penetration hole.

As shown in FIG. 2, the endo file 100 for dental endodontic treatment according to the embodiment of the present invention includes: a head portion 120 inserted into and detachably coupled to a hand piece 110, the head portion 120 provided on a upper portion of the endo file 100; a tissue removing portion 130 inserted, from a lower side of the head portion 120, into an inside of a root canal of a patient's tooth for removing a nerve of the tooth.

The endo file 100 according to the embodiment of the present invention further includes a connection portion 140 formed between the head portion 120 and the tissue removing portion 130. The connection portion 140 includes at least one horizontal penetration hole 152 so as to disperse stress generated during a rotation of the endo file 100. Thus, the connection portion 140 having at least one horizontal penetration hole 152 serves as a stress dispersion portion.

The endo file 100 according to the embodiment of the present invention is made of conventional materials, such as titanium, stainless steel, Ni—Ti (shape memory alloy), etc. that are excellent in corrosion resistance. The connection portion 140 transfers torque to the tissue removing portion 130 of the lower side of the connection portion 140 when the head portion 120 rotates by an operation of the hand piece 110.

Figure 3A:
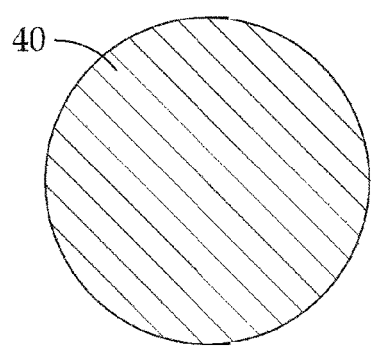
FIG. 3a is a sectional view of the conventional endo file showing a diameter of a solid core of the connection portion.
Figure 3B:
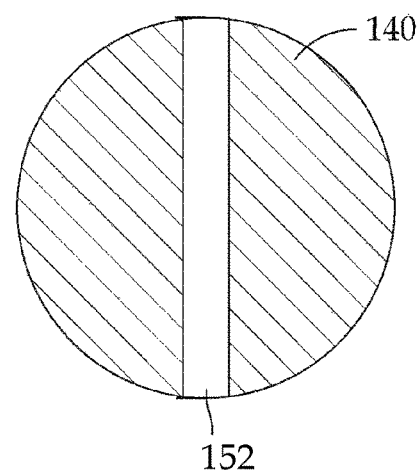
FIG. 3b is a sectional view of the endo file according to the present invention showing a structure of the stress dispersion portion that has the horizontal penetration hole formed in the connection portion.

The horizontal penetration hole 152 is provided in an inside of the connection portion 140, which is the stress dispersion portion, wherein the horizontal penetration hole 152 is formed by horizontally penetrating through the connection portion, dividing a cross-section of the connection portion 140 into two as shown in FIGS. 2 and 3b.

The respective cross-sections of the connection portion 140 that is divided into two sections are equal in size. When torque is transferred from the head portion 120, the torque is equally dispersed across the cross-sections of the connection portion 140 without concentration thereof on one cross-section, and is delivered to the tissue removing portion 130.

Figure 4A:
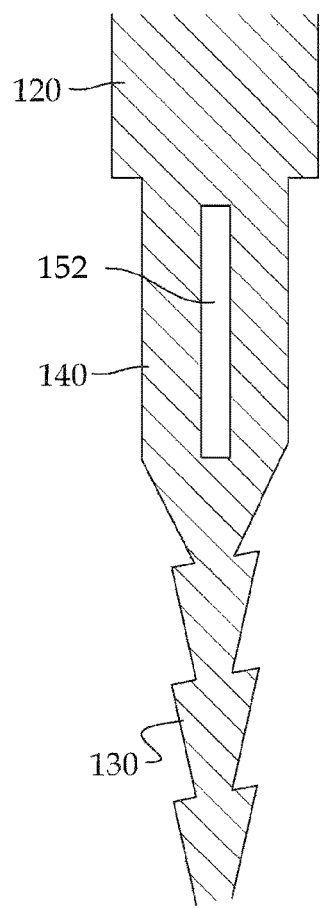
FIG. 4a is a sectional view of the endo file according to the present invention showing a structure of the horizontal penetration hole of the connection portion having a rectangular shape cross-section.
Figure 4B:
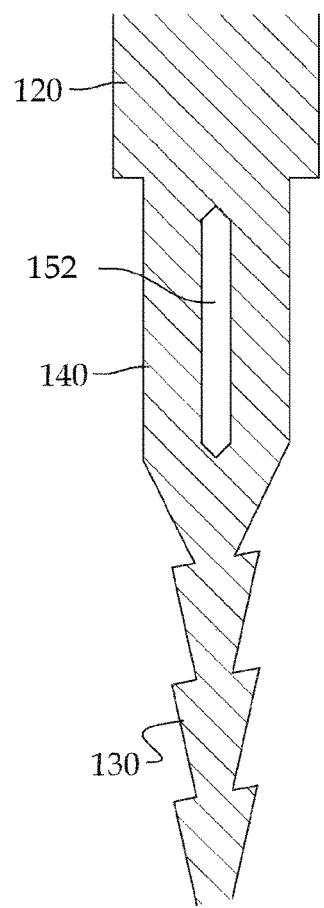
FIG. 4b is a sectional view of the endo file according to the present invention showing a structure of the horizontal penetration hole of the connection portion having a polygonal shape cross-section.
Figure 4C:
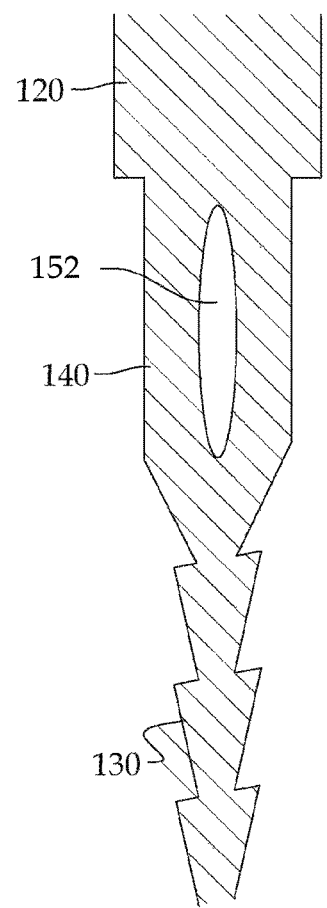
FIG. 4c is a sectional view of the endo file according to the present invention showing a structure of the horizontal penetration hole of the connection portion having an oval shape cross-section.

As shown in FIG. 4a, the horizontal penetration hole 152 of the stress dispersion portion may have a cross-section of a quadrilateral or a rectangular shape, but the present invention is not limited thereto. As shown in FIG. 4b, the horizontal penetration hole 152 may have a cross-section of a polygonal shape 152a, or an oval shape 152b as shown in FIG. 4c. In respect the shape of the cross-section mentioned above, the horizontal penetration hole 152 horizontally penetrates through the connection portion 140 in the same manner.

Figure 5A:
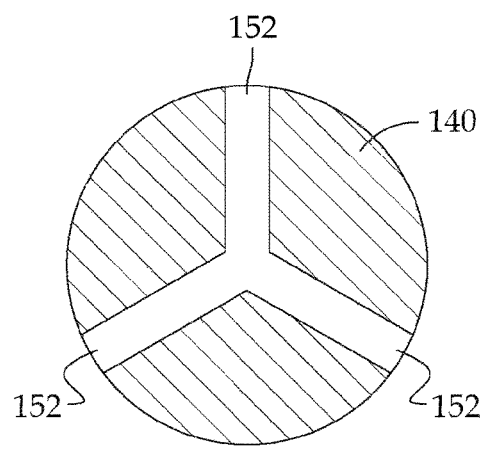
FIG. 5a is a sectional view of the endo file according to the present invention showing a structure of the cross-section of the connection portion equally divided into three sections.

Further, as shown in FIG. 2, the horizontal penetration hole 152 may be configured to divide the cross-section of the connection portion 140 into two sections. As shown in FIG. 5a, the horizontal penetration hole 152 may be configured to equally divide the cross-section of the connection portion 140 into three sections in a circumferential direction of a cross-section of the endo file 100.

Figure 5B:
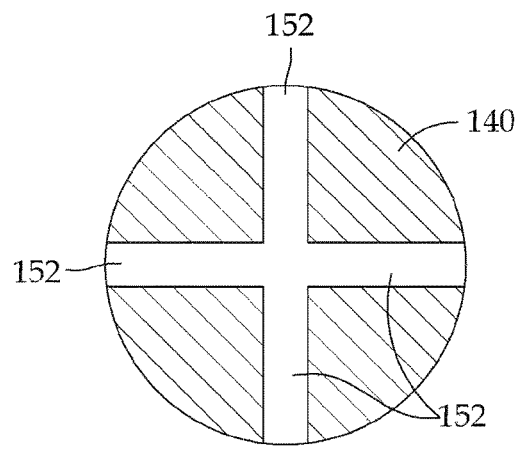
FIG. 5b is a sectional view of the endo file according to the present invention showing a structure of the horizontal penetration hole of the connection portion that is configured to be cruciform (+) and equally divides the cross-section of the connection portion into four sections.

Furthermore, as shown in FIG. 5b, the horizontal penetration hole 152 may be configured to equally divide the cross-section of the connection portion 140 into four sections, thereby making the cross-section of the connection portion 140 cruciform (+) shape.

Thus, even though the endo file faces high torque resistance in an inside of the root canal, the torque is equally dispersed across the cross-sections of the connection portion 140 without concentration thereof on one cross-section, and is delivered to the tissue removing portion 130.

Meanwhile, according to the embodiment of the present invention, the tissue removing portion, which consists of spiral elements and removes a nerve, may extend to the connection portion 140.

Further, the horizontal penetration hole 152 may be plural in number and is parallel to the connection portion 140. In this modified structure, as the horizontal penetration hole 152 is plural in number, the cross-section of the connection portion 140 is divided into more than three sections, and sizes of individual sections may be different from one another.

The horizontal penetration hole 152 provided in the stress dispersion portion generates a torsion buffer effect that buffers the torque transferred to the stress dispersion portion, like a torsion spring.

Figure 6:
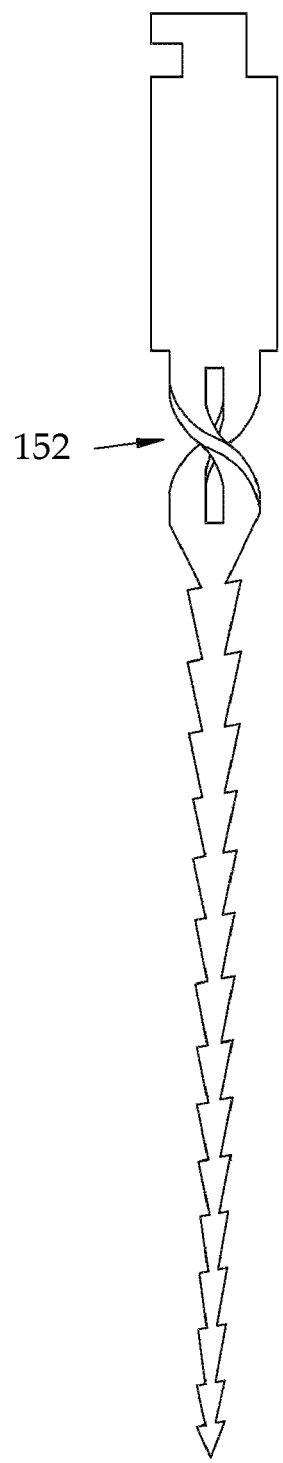
FIG. 6 is a referential view of the endo file according to the present invention showing torsion of the stress dispersion portion when excessive torque resistance is generated during use.

Thanks to a buffer structure mentioned above, the stress dispersion portion according to the embodiment of the present invention may prevent stress concentration in a specific area, whereby sudden breakage is prevented via prevention of an accumulation of fatigue. In addition, the endo file according to the embodiment of the present invention has the torsion spring effect that is mentioned above. Thus, as shown in FIG. 6, when too much torque resistance is generated during use of the endo file, the stress dispersion portion twists so that an operator can promptly recognize a twisted stress dispersion portion by naked eye. Therefore, it is possible to prevent the endo file from breaking.

In the endo file 100 for dental endodontic treatment configured by a description above according to the embodiment of the present invention, the endo file 100 is configured such that the head portion 120 is detachably inserted into the hand piece 110, and the head portion 120, the stress dispersion portion, and the tissue removing portion 130 rotate by an operation of the hand piece 110.

In this state, the tissue removing portion 130 is inserted into the root canal of a tooth, and removes the nerve of the tooth. In this process, the connection portion 140 delivers large torque transferred from the head portion 120 to the tissue removing portion 130 so as to remove the nerve of the tooth.

Here, the horizontal penetration hole 152 horizontally penetrates through the connection portion 140.

The horizontal penetration hole 152 equally divides the cross-section of the connection portion 140 into more than one section, for example, two to four sections having equal sizes respectively. Thus, the connection portion 140 having equally divided cross-sections disperses the torque transferred from the head portion 120, and delivers the torque to the tissue removing portion 130 without concentration thereof on one cross-section.

In particular, the horizontal penetration hole 152 of connection portion 140 generates a torsion buffer effect that buffers the torque transferred to the connection portion 140, like a torsion spring.

That is, in conventional solid core structure, the torque transferred from the head portion 120 is directly delivered to the tissue removing portion 130 without buffer. Thus, the tissue removing portion 130 is overloaded, and a fragile portion of the tissue removing portion 130 is broken due to the concentration of the stress thereon.

However, the connection portion 140 according to the embodiment of the present invention is capable of providing a space for allowing the horizontal penetration hole 152 to elastically deform the connection portion 140 by means of an external force, namely the torque. Thereby, sudden torque is not loaded onto the tissue removing portion 130, and a buffer effect is generated by elastic torsion deformation of the connection portion 140. Thus, the torque is smoothly delivered without the breakage of the tissue removing portion 130. According to the embodiment of the present invention, the connection portion 140 is configured to have a buffer structure so that the connection portion 140 can avoid the stress concentration, and prevent the sudden breakage of the endo file by preventing the accumulation of fatigue.

As described above, the endo file 100 for dental endodontic treatment according to the embodiment of the present invention, includes the stress dispersion portion provided in the connection portion 140, which is located between the head portion 120 and the tissue removing portion 130, the stress dispersion portion having at least one horizontal penetration hole so as to prevent and buffer the concentration of stress during the rotation of the endo file 100.

In other words, the stress dispersion portion provided in the connection portion 140 divides the cross-section of the connection portion 140 into more than one section due to at least one horizontal penetration hole 152 horizontally penetrating through the connection portion 140. Thereby, when the endo file 100 rotates in the root canal, stress is not concentrated on a portion of the connection portion 140 and the tissue removing portion 130. Thus, the torque is equally delivered from the head portion 120 to an end of the tissue removing portion 130, and thereby it is possible to effectively prevent the endo file 100 from breaking. Therefore, the endo file 100 is useful for effective dental endodontic treatment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. For instance, though the shape of a cross-section, and the number of the horizontal penetration holes 152 may be variable, they have the same effects respectively. However, simple modifications or modified structures fall within the scope and spirit of the invention as disclosed in the accompanying claims.

The invention claimed is:

1. An endo file for a dental endodontic treatment, the endo file comprising:
a head portion;
a tissue removing portion for removing nerves or diseased tissues within a tooth provided at a lower side of the head portion and having a long-narrow shape; and
a connection portion provided between the head portion and the tissue removing portion, wherein a stress dispersion portion is provided in the connection portion, the stress dispersion portion having at least one horizontal penetration hole to prevent stress concentration resulting from a resistance to a rotation of the tissue removing portion and to minimize endo file breakage,
wherein the horizontal penetration hole has a horizontal length which is smaller than a longitudinal length thereof and has closed ends at opposite sides along a longitudinal direction thereof,
wherein the connection portion and the tissue removing portion rotate around an axial direction due to the rotation of the head portion,
wherein the stress dispersion portion has a circular cross-section and the horizontal penetration hole passes through an axial center of the stress dispersion portion.

2. The endo file of claim 1, wherein the horizontal penetration hole has a quadrilateral, polygonal, cruciform or oval shape.

3. The endo file of claim 1, wherein a length of the tissue removing portion along a longitudinal direction of the endo file is greater than a length of the stress dispersion portion.

4. The endo file of claim 3, wherein a width of the stress dispersion portion along a direction perpendicular to a longitudinal direction of the endo file is equal to or greater than a width of the tissue removing portion.

5. The endo file of claim 1, wherein the cross-section of the stress dispersion portion is divided into two or more segments by the horizontal penetration hole, the two or more segments each having a substantially same cross-sectional area as an adjacent segment.

* * * * *